United States Patent [19]

Moore

[11] Patent Number: 5,466,877
[45] Date of Patent: Nov. 14, 1995

[54] PROCESS FOR CONVERTING PERFLUORINATED ESTERS TO PERFLUORINATED ACYL FLUORIDES AND/OR KETONES

[75] Inventor: George G. I. Moore, Afton, Minn.

[73] Assignee: Minnesota Mining and Manufacturing Company, St. Paul, Minn.

[21] Appl. No.: 213,109

[22] Filed: Mar. 15, 1994

[51] Int. Cl.⁶ .......................... C07C 51/58; C07C 53/00
[52] U.S. Cl. .......................... 562/852; 568/354
[58] Field of Search .......................... 562/852; 568/354

[56] References Cited

U.S. PATENT DOCUMENTS

| | | | |
|---|---|---|---|
| 3,900,372 | 8/1975 | Childs et al. | 204/81 |
| 5,093,432 | 3/1992 | Bierschenk et al. | 525/331.6 |

OTHER PUBLICATIONS

De Marco et al., J. Org. Chem. 37(21), 3332 (1972).
S. R. Sandler and W. Karo, *Organic Functional Group Preparations*, Second Edition, Academic Press, Inc., pp. 288–314, New York (1983).
M. Hudlicky, *Chemistry of Organic Fluorine Compounds*, Second Edition, Ellis Horwood, p. 325, New York (1992).
M. C. Sneed and R. C. Brasted, *Comprehensive Inorganic Chemistry*, vol. Six (The Alkali Metals), pp. 61–64, D. Van Nostrand Company, Inc., New York (1957).
H. Kobler et al., Justus Liebigs Ann. Chem. 1978, 1937.
L. O. Moore, J. Org. Chem. 35, 3999 (1970).
A. G. Pittman et al., J. Polymer Sci. A–1, 4, 2637 (1966).

*Primary Examiner*—Paul J. Killos
*Attorney, Agent, or Firm*—Gary L. Griswold; Walter N. Kirn; Lucy C. Weiss

[57] ABSTRACT

A process for converting perfluorinated carboxylic acid esters to perfluorinated acyl fluorides and/or perfluorinated ketones comprises the step of combining at least one perfluorinated carboxylic acid ester with at least one initiating reagent selected from the group consisting of gaseous, non-hydroxylic nucleophiles; liquid, non-hydroxylic nucleophiles; and mixtures of at least one non-hydroxylic nucleophile (gaseous, liquid, or solid) and at least one solvent which is inert to acylating agents. The process enables the dissociation of even high molecular weight, perfluorinated esters.

24 Claims, No Drawings

PROCESS FOR CONVERTING PERFLUORINATED ESTERS TO PERFLUORINATED ACYL FLUORIDES AND/OR KETONES

FIELD OF THE INVENTION

This invention relates to a process for preparing perfluorinated carboxylic acid fluorides and/or perfluorinated ketones.

BACKGROUND OF THE INVENTION

Many products of commercial value (such as oil-) and water-repellant finishes for textiles, paper, electronic articles, and the like; stain-repellant finishes for leather; and surfactants for a variety of applications) can be made from perfluorinated carboxylic acid fluorides (hereinafter, perfluorinated acyl fluorides) and perfluorinated ketones. Perfluorinated acyl fluorides can be prepared by electrochemical fluorination (ECF) of the corresponding hydrocarbon carboxylic acid (or a derivative thereof), using either anhydrous hydrogen fluoride (Simons ECF) or KF.2 HF (Phillips ECF) as the electrolyte. However, a drawback of Simons ECF is that side reactions often occur, and low purity and low yields are often obtained due to the formation of rearrangement and degradation products. Perfluorinated acyl fluorides can also be prepared from telomers of tetrafluoroethylene, but a characteristic of this method is that a distribution of molecular weights is obtained.

Although Phillips ECF (KF.2 HF) or direct fluorination ($F_2$) can be employed to reduce the occurrence of side reactions and provide high yields of a desired fluorinated product, hydrocarbon carboxylic acids cannot be fluorinated by such techniques without undergoing decarboxylation and/or other side reactions. Hydrocarbon carboxylic acid fluorides are extremely water-sensitive and difficult to handle, and hydrocarbon carboxylic acid chlorides yield chlorine-substituted fluorochemical products. In contrast, hydrocarbon carboxylic acid esters function well as starting compounds in both fluorination processes (see, e.g., U.S. Pat. Nos. 3,900,372 (Childs et al.) and 5,093,432 (Bierschenk et al.)), but, when hydrocarbon carboxylic acid esters are fluorinated, perfluorinated carboxylic acid esters (rather than perfluorinated acyl fluorides) are obtained. The perfluorinated esters are less useful than the corresponding acyl fluorides or ketones as intermediates in the preparation of commercial products, because perfluorinated esters, upon reaction with nucleophiles such as methanol, provide mixtures of products (derived from the acyl and the alkoxide portions of the perfluorinated ester) which may be difficult to separate. The side reactions of perfluorinated esters are especially limiting in making condensation polymers from difunctionals. Additional steps must therefore be undertaken to convert the perfluorinated esters to the more useful perfluorinated acyl fluorides and/or ketones.

U.S. Pat. No. 3,900,372 (Childs et al.) describes a combination process for the conversion of primary or secondary alkanols to perfluorinated acyl fluorides and/or perfluorinated ketones wherein said alkanols are esterified with acyl fluorides and the resulting partially fluorinated esters passed to an electrochemical fluorination step to produce perfluorinated esters which are thereafter cleaved on contacting with a source of fluoride ion under reacting conditions, e.g., a bed of a solid alkali metal fluoride catalyst at a temperature within the range of 80° C. to 220° C.

De Marco et al. disclose (in J. Org. Chem. 37(21), 3332 (1972)) that perfluorinated esters are decomposed in the presence of alkali metal fluorides at −78° C. or above, but note that for higher molecular weight esters the rate of decomposition at −78° C. is slow.

SUMMARY OF THE INVENTION

Briefly, this invention provides a process for converting even high molecular weight, perfluorinated carboxylic acid esters to perfluorinated acyl fluorides and/or perfluorinated ketones. The process comprises the step of combining at least one perfluorinated carboxylic acid ester with at least one initiating reagent selected from the group consisting of gaseous, non-hydroxylic nucleophiles; liquid, non-hydroxylic nucleophiles; and mixtures of at least one non-hydroxylic nucleophile (gaseous, liquid, or solid) and at least one solvent which is inert to acylating agents. As used herein, the terms "gaseous," "liquid," and "solid" refer to the physical state of the nucleophile under the conditions of temperature and pressure chosen for carrying out the process.

The process of the invention can be carried out at room temperature without the need for high temperature conditions and special high temperature equipment such as a hot tube. The process also avoids the problem of deactivation associated with the physical occlusion of solid catalysts by tar-forming contaminants of fluorination processes. Most importantly, the process of the invention enables the dissociation of high molecular weight, perfluorinated esters and is therefore preferably utilized for preparing perfluorinated acyl fluorides and/or perfluorinated ketones from perfluorinated esters having at least about six carbon atoms. The process is particularly useful for the preparation of alpha-branched perfluorinated acyl fluorides.

DETAILED DESCRIPTION OF THE INVENTION

Perfluorinated esters which can be utilized in the process of the invention are cyclic or acyclic, perfluorinated mono- or dicarboxylic acid esters derived from primary or secondary alcohols. Other classes of compounds which contain an ester moiety, e.g., carbonates and carbamates, can also be utilized, and, as used herein, the term "ester" includes such classes of compounds. The esters may contain small amounts of fluorinated material having one or a few residual hydrogen atoms, but are essentially fully fluorinated, i.e., perfluorinated. Preferably, the perfluorinated esters contain at least about six carbon atoms.

A class of perfluorinated esters which can be utilized in the process of the invention is that which can be represented by the following general formula:

$$R_f^1—(X)_nC(O)—O—R_f^2 \qquad (I)$$

wherein $R_f^1$ is selected from the group consisting of fluorine; linear, branched, and cyclic perfluoroalkyl groups which have from 1 to about 30 carbon atoms; linear, branched, and cyclic perfluoroalkyl groups which have from 1 to about 30 carbon atoms and which contain at least one catenary, i.e., in-chain, heteroatom (preferably, at least one catenary ether oxygen atom); and linear, branched, and cyclic perfluoroalkylene groups which have from 1 to about 30 carbon atoms and which are bonded to $R_f^2$ or to an $R_f^3$ group of X to form a cyclic structure; $R_f^2$ is selected from the group consisting of linear, branched, and cyclic, primary and secondary perfluoroalkyl groups which have from 1 to about 30 carbon atoms; linear, branched, and cyclic, primary and secondary perfluoroalkyl groups which have from 1 to about 30 carbon atoms and which contain at least one catenary heteroatom (preferably, at least one catenary ether oxygen atom); and linear, branched, and cyclic, primary and secondary perfluoroalkylene groups which have from 1 to about 30 carbon atoms and which are bonded to $R_f^1$ to form a cyclic structure; X is selected from the group consisting of —O— and —$NR_f^3$—, wherein $R_f^3$ is selected from the group defined above for $R_f^1$, with the proviso that when $R_f^3$ is perfluoroalkylene it is bonded to $R_f^1$; n is an integer of 0 or 1; and wherein $R_f^1$ or $R_f^2$ can further contain an ester moiety. A preferred subclass of perfluorinated esters is that represented by general formula I above, wherein $R_f^1$ and $R_f^2$ each contain from 1 to about 18 carbon atoms and wherein the sum of the number of carbon atoms in $R_f^1$ and the number of carbon atoms in $R_f^2$ is at least about 6.

Representative examples of suitable perfluorinated esters include the following compounds:

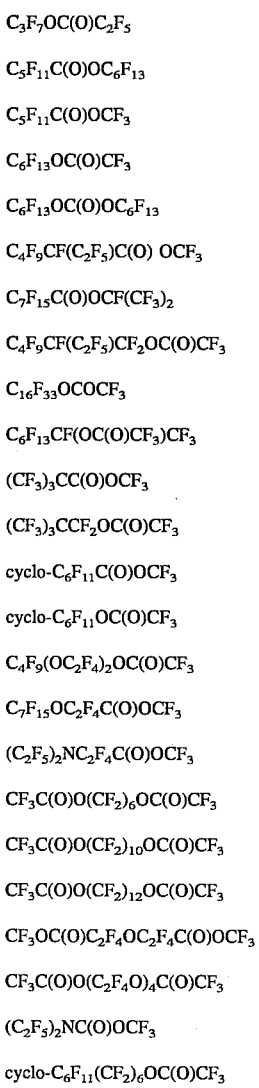

$C_3F_7OC(O)C_2F_5$ $C_5F_{11}C(O)OC_6F_{13}$ $C_5F_{11}C(O)OCF_3$ $C_6F_{13}OC(O)CF_3$ $C_6F_{13}OC(O)OC_6F_{13}$ $C_4F_9CF(C_2F_5)C(O)\ OCF_3$ $C_7F_{15}C(O)OCF(CF_3)_2$ $C_4F_9CF(C_2F_5)CF_2OC(O)CF_3$ $C_{16}F_{33}OCOCF_3$ $C_6F_{13}CF(OC(O)CF_3)CF_3$ $(CF_3)_3CC(O)OCF_3$ $(CF_3)_3CCF_2OC(O)CF_3$ cyclo-$C_6F_{11}C(O)OCF_3$ cyclo-$C_6F_{11}OC(O)CF_3$ $C_4F_9(OC_2F_4)_2OC(O)CF_3$ $C_7F_{15}OC_2F_4C(O)OCF_3$ $(C_2F_5)_2NC_2F_4C(O)OCF_3$ $CF_3C(O)O(CF_2)_6OC(O)CF_3$ $CF_3C(O)O(CF_2)_{10}OC(O)CF_3$ $CF_3C(O)O(CF_2)_{12}OC(O)CF_3$ $CF_3OC(O)C_2F_4OC_2F_4C(O)OCF_3$ $CF_3C(O)O(C_2F_4O)_4C(O)CF_3$ $(C_2F_5)_2NC(O)OCF_3$ cyclo-$C_6F_{11}(CF_2)_6OC(O)CF_3$ Perfluorinated esters suitable for use in the process of the invention can be prepared by either the direct fluorination or the electrochemical fluorination of the corresponding hydrocarbon or partially-fluorinated carboxylic acid esters, as described, e.g., in U.S. Pat. Nos. 5,093,432 (Bierschenk et al.) and 3,900,372 (Childs et al.), the descriptions of which are incorporated herein by reference. Suitable hydrocarbon precursors for use in direct or electrochemical fluorination can be prepared by the reaction of alcohols and carboxylic acids (or derivatives thereof, e.g., carboxylic acid chlorides), by the alcoholysis of nitriles, and by other known methods (see, e.g., S. R. Sandler and W. Karo, *Organic Functional Group preparations*, Second Edition, Academic Press, Inc., pages 288–314, New York (1983)). Suitable partially-fluorinated precursors can be prepared, e.g., by the reaction of alcohols with partially-fluorinated or perfluorinated carboxylic acids (or derivatives thereof), as described, e.g., in U.S. Pat. No. 3,900,372 (Childs), and by the reaction of partially-fluorinated alcohols with carboxylic acids (or derivatives thereof), as described, e.g., by M. Hudlicky, *Chemistry of Organic Fluorine Compounds*, Second Edition, Ellis Horwood, page 325, New York (1992).

Perfluorinated esters suitable for use in the process of the invention can also be prepared by the reaction of perfluoroacyl fluorides with alkali metal perfluoroalkoxides, as described by De Marco et al. in J. Org. Chem. 37 (21), 3332 (1972).

Initiating reagents which can be employed in the process of the invention are those gaseous or liquid, non-hydroxylic nucleophiles and mixtures of gaseous, liquid, or solid, non-hydroxylic nucleophile(s) and solvent (hereinafter termed "solvent mixtures") which are capable of nucleophilic reaction with the perfluorinated esters. A wide variety of materials with modest to strong nucleophilic properties possess such capability and initiate an apparent fluoride-propagated dissociation of the perfluorinated esters into two perfluoroacyl components. The presence of small amounts of hydroxylic nucleophiles can be tolerated.

Suitable gaseous or liquid, non-hydroxylic nucleophiles for use in the process of the invention include dialkylamines, trialkylamines, carboxamides, alkyl sulfoxides, amine oxides, oxazolidones, pyridines, and the like, and mixtures thereof. Suitable non-hydroxylic nucleophiles for use in solvent mixtures include such gaseous or liquid, non-hydroxylic nucleophiles, as well as solid, non-hydroxylic nucleophiles, e.g., fluoride, cyanide, cyanate, iodide, chloride, bromide, acetate, mercaptide, alkoxide, thiocyanate, azide, trimethylsilyl difluoride, bisulfite, and bifluoride anions, which can be utilized in the form of alkali metal, ammonium, alkyl-substituted ammonium (mono-, di-, tri-, or tetra-substituted), or quaternary phosphonium salts, and mixtures thereof. Such salts are in general commercially available but, if desired, can be prepared by known methods, e.g., those described by M. C. Sneed and R. C. Brasted in *Comprehensive Inorganic Chemistry*, Volume Six (The Alkali Metals), pages 61–64, D. Van Nostrand Company, Inc., New York (1957), and by H. Kobler et al. in Justus Liebigs Ann. Chem. 1978, 1937. 1,4-diazabicyclo[2.2.2] octane and the like are also suitable solid nucleophiles.

Representative examples of suitable gaseous or liquid, non-hydroxylic nucleophiles include trimethylamine, triethylamine, dimethylformamide, dimethylsulfoxide, N-methyl-2-oxazolidone, pyridine, lutidine, quinoline, and mixtures thereof. Trimethylamine, triethylamine, pyridine, and dimethylformamide (and mixtures thereof) are preferred due to their ready availability.

Representative examples of suitable solid, non-hydroxylic nucleophiles include the fluoride, cyanide, cyanate, iodide, chloride, bromide, acetate, mercaptide, alkoxide, thiocyanate, azide, trimethylsilyl difluoride, bisulfite, and bifluoride salts of lithium, sodium, potassium, ammonium, alkyl-substituted ammonium (where the alkyl group(s) have from one to about ten carbon atoms), tris(dimethylamino)sulfonium, and tetraaryl phosphonium (where the aryl groups are phenyl or substituted phenyl); 1,4-diazabicyclo

[2.2.2]octane; and mixtures thereof. The preferred anions for use in the process of the invention are fluoride and chloride (due to considerations of cost, availability, and product purity), and these anions are preferably utilized in the form of potassium, sodium, ammonium, or alkyl-substituted ammonium salts, or mixtures thereof.

Fluoride ion is the most preferred nucleophile (preferably, in the form of the potassium salt, which is inexpensive and readily available) because it produces acyl fluoride directly, whereas other nucleophiles apparently produce contaminatory and/or yield-reducing by-products.

The above-cited nucleophiles have the indicated physical states under ambient or room temperature conditions. Since physical states vary with temperature, these or other nucleophiles may be suitable for use at other temperatures, as is known by those skilled in the art.

Solvents which can be utilized in the process of the invention are those which are inert to acylating agents. Such solvents include polar, aprotic solvents. Representative examples of polar, aprotic solvents include acyclic ethers such as diethyl ether, ethylene glycol dimethyl ether, and diethylene glycol dimethyl ether; cyclic ethers such as tetrahydrofuran, 2-methyltetrahydrofuran, dioxane, dioxolane, and 4-methyldioxolane; ketones such as acetone and 2-butanone; carboxylic acid esters such as methyl formate, ethyl formate, methyl acetate, diethyl carbonate, propylene carbonate, ethylene carbonate, and butyrolactones; nitriles such as acetonitrile and benzonitrile; nitro compounds such as nitromethane or nitrobenzene; alkyl amides such as N,N-dimethylformamide, N,N-diethylformamide, and N-methylpyrrolidone; alkyl sulfones such as dimethylsulfone, tetramethylene sulfone, and other sulfolanes; oxazolidones such as N-methyl-2-oxazolidone; and mixtures thereof.

Nonpolar, aprotic solvents (e.g., alkanes and arenes) can also be utilized in the process of the invention in admixture with phase transfer catalyst(s). Representative examples of such solvent/catalyst combinations include toluene/crown ether, e.g., 18-crown-6; toluene/tetraalkylammonium halide, e.g., tetrabutylammonium fluoride; benzene/tetraarylphosphonium halide, e.g., tetraphenylphosphonium chloride; heptane/crown ether, and the like; and mixtures thereof. If desired, polar, aprotic solvent can be mixed with nonpolar, aprotic solvent or with a mixture of nonpolar, aprotic solvent and phase transfer catalyst.

Preferred solvents include diethylene glycol dimethyl ether, acetonitrile, acetone, toluene/crown ether, toluene/tetraalkylammonium fluoride, and mixtures thereof. Acetonitrile, diethylene glycol dimethyl ether, toluene/tetraalkylammonium fluoride, and mixtures thereof are most preferred due to their relatively low cost and/or ease of drying.

The process of the invention can be carried out by introducing at least one perfluorinated ester and at least one initiating reagent (which may comprise at least one solvent component, in addition to at least one nucleophile component) to a vessel, which can be an open or closed vessel, and which preferably is a stirred reactor connected to separation means (e.g., condenser(s) and/or trap(s)) for isolating volatile reaction products and enabling their removal or recycle. The ester and the component(s) of the initiating reagent can be introduced to the vessel separately or in any manner of combination, and in any order. When the process is carried out on a small scale, the ester can be conveniently added to the vessel first, and the component(s) of the initiating reagent then combined and added to the vessel. The contents of the vessel is preferably agitated to facilitate mixing.

The process of the invention can be generally carried out at a temperature in the range of from about 0° C. to about 100° C. (depending, e.g., on the reaction rate desired), but, for convenience, is preferably carried out under room temperature conditions. The nucleophile component (or components) of the initiating reagent is used in an amount sufficient to initiate the dissociation of the perfluorinated ester. This amount is generally a substoichiometric amount, e.g., amounts as low as a few milligrams of nucleophile per 100 grams of perfluorinated ester have been found to be effective. The solvent component (or components) of the initiating reagent, if any, is utilized in an amount sufficient to wet the surface of solid nucleophile. Both the reaction conditions and the proportions of ester, nucleophile, and solvent can vary widely.

The process of the invention can be carried out continuously (e.g., by continuously feeding perfluorinated ester to the vessel and continuously withdrawing perfluorinated product from the vessel), semi-continuously (e.g., by continuously feeding ester and intermittently withdrawing product, or by intermittently feeding ester and continuously withdrawing product), or batchwise. Depending upon the degree of purity of the perfluorinated ester, a single addition of an initiating amount of nucleophile can be sufficient or subsequent replenishment can be necessary. The process can be carried out with recycle of at least a portion of the product perfluorinated acyl fluoride(s) (resulting from the dissociation of the perfluorinated ester) for use in preparing partially-fluorinated esters which can be fluorinated to provide additional perfluorinated ester for use in the process.

The process of the invention enables the conversion of even high molecular weight, perfluorinated carboxylic acid esters to perfluorinated acyl fluorides and/or perfluorinated ketones. The types of pefluorinated products which are obtained in a particular case are dependent upon the nature of the starting ester, in that esters derived from primary alkanols provide different products from those derived from secondary alkanols, as shown by the following general reaction schemes:

Primary: 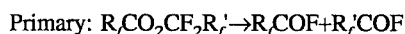

Secondary: 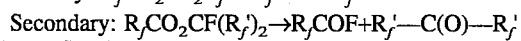

The perfluorinated products of the process of the invention can be recovered by, e.g., draining and can then be separated and purified by, e.g., distillation, if desired.

The process of the invention can be carried out at room temperature without the need for high temperature conditions and special high temperature equipment such as a hot tube. The process also avoids the problem of deactivation associated with the physical occlusion of solid catalysts by tar-forming contaminants of fluorination processes. The process is particularly useful for the preparation of alpha-branched perfluorinated acyl fluorides. The perfluorinated products of the process are useful as reactive intermediates for the preparation of monomers, surfactants, and other materials such as textile treating agents, paper treating agents, and potting compounds.

This invention is further illustrated by the following examples, but the particular materials and amounts thereof recited in these examples, as well as other conditions and details, should not be construed to unduly limit this invention.

EXAMPLES

Example 1

Dissociation of n-$C_6F_{13}O(CO)CF_3$ Using a Mixture of Potassium Fluoride and Triglyme A partially-fluorinated precursor ester, n-$C_6H_{13}O(CO)CF_3$, was prepared by treatment of 510 g of n-hexanol with 450 mL of trifluoroacetic acid and 50 mL of concentrated $H_2SO_4$, with overnight stirring at 23° C. 97 g of the precursor was fluorinated with $F_2$ in Freon™ 113 (1,1,2-trichloro-1,2,2-trifluoroethane, available from DuPont) using the procedure taught in U.S. Pat. No. 5,093,432 (Bierschenk et al.) to produce perfluorinated ester, n-$C_6F_{13}O(CO)CF_3$. The Freon™ 113 solution of the ester was stripped of solvent using a three-plate Snyder column to yield 134.2 g of crude perfluorinated ester product. The product was mixed with 30 mL of triglyme (triethyleneglycol dimethyl ether) to which 2 g of KF had been added. Gas (presumed to be trifluoroacetyl fluoride) was immediately evolved, but was not collected. The liquid product, perfluorohexanoyl fluoride, was then distilled to yield 46.2 g of n-$C_5F_{11}COF$ having a boiling range of 60°–64° C. Samples of the gas and of the liquid product were treated with methanol to provide the methyl esters $CF_3C(O)OCH_3$ and n-$C_5F_{11}C(O)OCH_3$, confirmed by gas chromatographic (GC) analysis.

Comparative Example 1

Attempted Dissociation of n-$C_{10}F_{21}O(CO)CF_3$ Using Solid Sodium Fluoride

Perfluoro(decyl acetate), n-$C_{10}F_{21}O(CO)CF_3$, was prepared by direct fluorination of 71.2 g of decyl trifluoroacetate, using essentially the procedure of Example 1. 155.2 g of the neat perfluorinated ester was heated to about 150° C. with no change, was cooled, and was then treated with 2 g of solid NaF, but no evolution of gas was observed, indicating that the ester was not cleaved under these conditions. The resulting mixture was then heated to 150° C. for approximately 2 hours without any gas evolution. This comparative example shows that higher molecular weight perfluorinated esters such as perfluoro(decyl acetate) may not cleave upon contact with solid, non-hydroxylic nucleophile in the absence of solvent, even when heated to temperatures well above room temperature.

Example 2

Dissociation of $C_4F_9O(C_2F_4O)_2(CO)CF_3$ Using a Mixture of Potassium Fluoride and Diglyme $C_4F_9O(C_2F_4O)_2(CO)CF_3$ was prepared by direct fluorination of 100 g of $C_4H_9O(C_2H_4O)_2(CO)CH_3$ by essentially the procedure of Example 1. To 243 g of the resulting crude perfluorinated ester was added 0.5 g of KF in 1 g of diglyme. Gas evolution was observed, indicating ester cleavage. The resulting product was purified by distillation to yield 144.6 g of $C_4F_9OC_2F_4OCF_2COF$, boiling at 105°–110° C.

Example 3

Dissociation of Perfluoro(methyl cyclohexanoate) Using a Mixture of Potassium Fluoride and Diglyme Perfluoro(methyl cyclohexanoate) was prepared by direct fluorination of methyl benzoate, using essentially the procedure of Example 1. To 504 g of the crude perfluorinated ester (assayed at 60% by GC analysis of the methyl ester) was added 1 g of KF in 10 mL of diglyme. After rapid evolution of gas (presumed to be carbonyl fluoride) was complete, the resulting product was distilled to yield 150.5 g of perfluorocyclohexane carbonyl fluoride, boiling at 78–90° C.

Example 4

Dissociation of $CF_3OC_3F_6OCF_2CF(OC(O)CF_3)CF_3$ Using a Mixture of Potassium Fluoride and Diglyme $CF_3OC_3F_6OCF_2CF(OC(O)CF_3)CF_3$ was prepared by direct fluorination of 100 g of dipropyleneglycol methyl ether acetate using essentially the procedure of Example 1. The resulting solution of crude perfluorinated ester was concentrated to 142 g by evaporation of most of the solvent. The resulting concentrate was treated with 0.2 g of KF in 2 mL of diglyme, resulting in vigorous evolution of gas (presumed to be trifluoroacetyl fluoride). When gas evolution ceased, the resulting product was distilled using a 6-inch Vigreux column to yield 88.9 g of perfluorinated ketone, $CF_3OC_3F_6OCF_2C(O)CF_3$, boiling at 85° C. The product was confirmed by IR analysis.

Example 5

Dissociation of Perfluoro($\epsilon$-caprolactone) Using Pyridine

Perfluoro($\epsilon$-caprolactone) was prepared by direct fluorination of 97.3 g of $\epsilon$-caprolactone using essentially the procedure of Example 1. The resulting solution of crude perfluorinated ester was concentrated to about 300 g by evaporation of most of the solvent. A 50 g sample of the resulting concentrate was treated with 2 drops of pyridine, resulting in a moderate exotherm and complete conversion of the ester to perfluoroadipoyl fluoride, as confirmed by IR and GC analysis of the dimethyl ester.

Example 6 and Comparative Example 2

Dissociation of Perfluoro(dimethyl tricyclo[1.1.1]pentane-1,3-dicarboxylate) Using a Mixture of Potassium Fluoride and Diglyme and a Mixture of Potassium Iodide and Acetone Perfluoro(dimethyl tricyclo[1.1.1]pentane-1,3-dicarboxylate) was prepared by direct fluorination of dimethyl tricyclo[1.1.1]pentane-1,3-dicarboxylate, using essentially the procedure of Example 1. About 1 mL of the neat perfluorinated ester was first shaken with approximately 10 mg of solid KF as a comparative example, and no gas evolution was observed. A drop of diglyme was then added to the mixture of ester and KF (according to the process of the invention), and evolution of gas (presumed to be carbonyl fluoride) ensued. Cleavage of the diester to the diacyl fluoride was confirmed by IR analysis.

The above procedure was repeated using about 5 drops of a 5% (weight to volume) solution of KI in acetone and about 1 mL of the ester. Again, evolution of gas (presumed to be carbonyl fluoride) was observed, and cleavage was confirmed by IR analysis.

Example 7

Dissociation of Perfluoro(hexanediol diacetate) Using Pyridine

Perfluoro(hexanediol diacetate) was prepared by direct fluorination of hexanediol diacetate, using essentially the procedure of Example 1. The resulting crude perfluorinated diester was concentrated by evaporation of solvent. One mL of the concentrated diester was treated with one drop of pyridine, and immediate evolution of gas (presumed to be trifluoroacetyl fluoride) was observed. Complete conversion of the perfluorinated diester to the perfluorinated diacyl fluoride, perfluoroadipoyl fluoride, was confirmed by IR analysis.

Examples 8–11 and Comparative Examples 3–6

Dissociation of Various Perfluorinated Esters Using a Mixture of Potassium Fluoride and Diglyme A number of additional perfluorinated esters were cleaved using the process of the invention. In each case, a small sample (about 1 mL) of the neat ester was first shaken with a few milligrams of solid KF (in a glass vial) as a comparative example. No gas evolution was observed for any of the esters, so a drop of diglyme was then added to the mixture of ester and KF (according to the process of the invention), and the resulting mixture was shaken. In each case, gas evolution was then observed and was taken as evidence that the ester had been cleaved to acyl fluoride. Such cleavage was confirmed by IR analysis. The perfluorinated esters cleaved are listed in Table 1 below:

TABLE 1

| Example No. | Perfluorinated Ester |
| --- | --- |
| 8 | n-$C_{10}F_{21}O(CO)CF_3$ |
| 9 | $(CF_3)_3CC(O)OCF_3$ |
| 10 | 4-Cl-cyclo-$C_6F_{10}OC(O)CF_3$ |
| 11 | $C_4F_9CF(C_2F_5)CF_2OC(O)CF_3$ |

Example 12

Dissociation of $C_6F_{13}CF[OC(O)CF_3]CF_3$ Using a Mixture of Potassium Fluoride and Diglyme $C_6F_{13}CF[OC(O)CF_3]CF_3$ was prepared by direct fluorination of 100 g of 2-octyl acetate, using essentially the procedure of Example 1. The resulting crude perfluorinated ester was distilled to provide 267 g of perfluorinated ester, to which a mixture of 2.0 g of KF and 5 mL of diglyme was added. Gas evolution was observed. The resulting mixture was stirred overnight and then distilled to yield 151.5 g of perfluoro(2-octanone), boiling at 101°–109° C. The product was confirmed by IR analysis.

Examples 13–27 and Comparative Examples 7–12

Dissociation of Perfluoro(nonyl acetate) Using Various Different Initiating Reagents A partially-fluorinated precursor ester, nonyl trifluoroacetate, was prepared by dropwise addition of 170 mL of trifluoroacetic acid to 290 g of n-nonanol, followed by addition of 22 mL of concentrated $H_2SO_4$. The resulting mixture was stirred at 60° C. overnight. The stirred mixture was then cooled, the resulting organic phase was collected, and partially-fluorinated ester product was isolated by distillation (bp 49°–56° C./0.1 torr). The product was then fluorinated in Freon™ 113 by essentially the procedure of Example 1 to provide perfluoro(nonyl acetate), $C_9F_{19}O(CO)CF_3$.

A number of different initiating reagents were evaluated by adding a small amount of reagent to approximately 1 mL of neat perfluoro(nonyl acetate). The "small amount" was a few milligrams for solid reagents, a drop for liquid or solution reagents, and a few small bubbles for gaseous reagents. Cleavage of the perfluorinated ester to perfluorononanoyl fluoride was first determined by observed gas evolution (presumed to be trifluoroacetyl fluoride) and was then verified by IR analysis. The results of the evaluations are shown in Table 2 below and indicate that perfluorinated esters can be cleaved by a variety of initiating reagents comprising non-hydroxylic nucleophile in gaseous, liquid, or solvent mixture form.

TABLE 2

| Example No. | Initiating Reagent | Cleavage to $C_8F_{17}COF$ |
| --- | --- | --- |
| 13 | $(C_2H_5)_3N$ | Yes |
| 14 | Pyridine | Yes |
| 15 | Dimethylformamide | Yes |
| Comparative 7 | NaF | No |
| 16 | NaF/Diglyme | Yes |
| Comparative 8 | $NH_4F$ | No |
| 17 | $NH_4F/CH_3CN$ | Yes |
| 18 | NaI/Acetone | Yes |
| 19 | $NaN_3$/Acetone | Yes |
| 20 | $NaF/CH_3CN$ | Yes |
| 21 | KF/18-crown-6 Ether/Toluene | Yes |
| 22 | NaCl/18-crown-6 Ether/Benzene | Yes |
| 23 | KBr/18-crown-6 Ether/Benzene | Yes |
| 24 | $(CH_3)_2NH$ | Yes |
| Comparative 9 | $CH_3CN$ | No |
| Comparative 10 | Water | No |
| Comparative 11 | Methanol | No |
| Comparative 12 | Ethanol | No |
| 25 | Ethyl oxazoline | Yes |
| 26 | Adogen™ 464* | Yes |
| 27 | Sodium Acetate/Acetone | Yes |

*Adogen™ 464 is a mixture of methyl trialkyl ($C_8$–$C_{10}$) ammonium chlorides available from Aldrich Chemical Company.

Various modifications and alterations of this invention will become apparent to those skilled in the art without departing from the scope and spirit of this invention.

I claim:

1. A process for converting perfluorinated carboxylic acid esters to perfluorinated acyl fluorides and/or perfluorinated ketones comprising the step of combining at least one perfluorinated carboxylic acid ester with at least one initiating reagent selected from the group consisting of gaseous, non-hydroxylic nucleophiles; liquid, non-hydroxylic nucleophiles; and mixtures of at least one non-hydroxylic nucleophile and at least one solvent which is inert to acylating agents.

2. The process of claim 1 wherein said ester has at least about six carbon atoms.

3. The process of claim 1 wherein said ester is selected from the group represented by the general formula

$$R_f^1-(X)_n-C(O)-O-R_f^2 \qquad (I)$$

wherein $R_f^1$ is selected from the group consisting of fluorine; linear, branched, and cyclic perfluoroalkyl groups which have from 1 to about 30 carbon atoms; linear, branched, and cyclic perfluoroalkyl groups which have from 1 to about 30 carbon atoms and which contain at least one catenary heteroatom; and linear, branched, and cyclic perfluoroalkylene groups which have from 1 to about 30 carbon atoms and which are bonded to $R_f^2$ or to an $R_f^3$ group of X to form a cyclic structure; said $R_f^2$ is selected from the group consisting of linear, branched, and cyclic, primary and secondary perfluoroalkyl groups which have from 1 to about 30 carbon atoms; linear, branched, and cyclic, primary and secondary perfluoroalkyl groups which have from 1 to about 30 carbon atoms and which contain at least one catenary heteroatom; and linear, branched, and cyclic, primary and secondary perfluoroalkylene groups which have from 1 to about 30 carbon atoms and which are bonded to said $R_f^1$ to form a cyclic structure; said X is selected from the group consisting of —O— and —$NR_f^3$—, wherein $R_f^3$ is selected from the group defined above for said $R_f^1$, with the proviso that when said $R_f^3$ is perfluoroalkylene it is bonded to said $R_f^1$; and n is an integer of 0 or 1.

4. The process of claim 3 wherein said $R_f^1$ or said $R_f^2$ further contains an ester moiety 5. The process of claim 3 wherein said heteroatom is an ether oxygen atom.

6. The process of claim 3 wherein said $R_f^1$ and said $R_f^2$ each contain from 1 to about 18 carbon atoms and wherein the sum of the number of carbon atoms in said $R_f^1$ and the number of carbon atoms in said $R_f^2$ is at least about 6.

7. The process of claim 3 wherein said ester is selected from the group consisting of n-$C_6F_{13}O(CO)CF_3$, $C_4F_9O(C_2F_4O)_2(CO)CF_3$, perfluoro(methyl cyclohexanoate), $CF_3OC_3F_6OCF_2CF(OC(O)CF_3)CF_3$, perfluoro(ε-caprolactone), perfluoro (dimethyl tricyclo [1.1.1]pentane-1,3-dicarboxylate), perfluoro(hexanediol diacetate), n-$C_{10}F_{21}O(CO)CF_3$, $(CF_3)_3CCO_2CF_3$, 4-Cl-cyclo-$C_6F_{10}OC(O)$ $CF_3$, $C_4F_9CF(C_2F_5)CF_2OC(O)CF_3$, $C_6F_{13}CF[OC(O)CF_3]CF_3$, and perfluoro(nonyl acetate).

8. A process for converting perfluorinated carboxylic acid esters to perfluorinated acyl fluorides and/or perfluorinated ketones comprising the step of combining at least one perfluorinated carboxylic acid ester with at least one initiating reagent selected from the group consisting of dialkylamines, trialkylamines, carboxamides, alkyl sulfoxides, amine oxides, oxazolidones, pyridines, mixtures thereof, and mixtures of at least one thereof and at least one solvent which is inert to acylating agents.

9. The process of claim 8 wherein said initiating reagent is selected from the group consisting of trimethylamine, triethylamine, dimethylformamide dimethylsulfoxide, N-methyl-2-oxazolidone, pyridine, lutidine, quinoline, mixtures thereof, and mixtures of at least one thereof and at least one said solvent.

10. A process for converting perfluorinated carboxylic acid esters to perfluorinated acyl fluorides and/or perfluorinated ketones comprising the step of combining at least one perfluorinated carboxylic acid ester with at least one initiating reagent selected from the group consisting of mixtures of at least one compound, selected from the group consisting of 1,4-diazabicyclo[2.2.2]octane and the alkali metal, ammonium, alkyl-substituted ammonium, tris(dimethylamino)sulfonium, and quaternary phosphonium salts of fluoride, cyanide, cyanate, iodide, chloride, bromide, acetate, mercaptide, alkoxide, thiocyanate, azide, trimethylsilyl difluoride, bisulfite, and bifluoride anions, and at least one solvent which is inert to acylating agents.

11. The process of claim 10 wherein said initiating reagent is selected from the group consisting of mixtures of at least one salt, selected from the group consisting of the lithium, sodium, potassium, ammonium, alkyl-substituted ammonium, tris(dimethylamino)sulfonium, and tetraaryl phosphonium salts of said anions, and at least one said solvent.

12. The process of claim 10 wherein said anions are selected from the group consisting of chloride and fluoride.

13. The process of claim 12 wherein said anions are fluoride.

14. A process for converting perfluorinated carboxylic acid esters to perfluorinated acyl fluorides and/or perfluorinated ketones comprising the step of combining at least one perfluorinated carboxylic acid ester with at least one initiating reagent selected from the group consisting of gaseous non-hydroxylic nucleophiles; liquid, non-hydroxylic nucleophiles; and mixtures of at least one non-hydroxylic nucleophile and at least one solvent selected from the group consisting of polar, aprotic solvents; mixtures of at least one nonpolar, aprotic solvent and at least one phase transfer catalyst; mixtures of at least one polar, aprotic solvent and at least one nonpolar, aprotic solvent; and mixtures thereof.

15. The process of claim 14 wherein said polar, aprotic solvent is selected from the group consisting of acyclic ethers, cyclic ethers, ketones, carboxylic acid esters, nitriles, nitro compounds, alkyl amides, alkyl sulfones, oxazolidones, and mixtures thereof.

16. The process of claim 14 wherein said nonpolar, aprotic solvent is selected from the group consisting of alkanes, arenes, and mixtures thereof.

17. The process of claim 14 wherein said phase transfer catalyst is selected from the group consisting of crown ethers, tetraalkylammonium halides, tetraarylphosphonium halides, and mixtures thereof.

18. The process of claim 14 wherein said solvent is selected from the group consisting of diethylene glycol dimethyl ether, acetonitrile, acetone, mixtures of toluene and crown ether, mixtures of toluene and tetraalkylammonium halide, and mixtures thereof.

19. A process for converting perfluorinated carboxylic acid esters to perfluorinated acyl fluorides and/or perfluorinated ketones comprising the step of combining at least one perfluorinated carboxylic acid ester with a substoichiometric amount of at least one initiating reagent selected from the group consisting of gaseous, non-hydroxylic nucleophiles liquid, non-hydroxylic nucleophiles; and mixtures of at least one non-hydroxylic nucleophile and at least one solvent which is inert to acylating agents.

20. The process of claim 1 carried out at a temperature in the range of from about 0° C. to about 100° C.

21. The process of claim 20 wherein said temperature is room temperature.

22. The process of claim 1 further comprising the step of recovering the resulting perfluorinated product.

23. The process of claim 1 further comprising the step of recycling at least a portion of the resulting perfluorinated product.

24. A process for converting perfluorinated carboxylic acid esters to perfluorinated acyl fluorides and/or perfluorinated ketones comprising the step of combining at least one perfluorinated carboxylic acid ester having at least about six carbon atoms with at least one initiating reagent selected from the group consisting of trimethylamine; triethylamine; pyridine; dimethylformamide; mixtures of at least one salt, selected from the group consisting of the potassium, sodium, ammonium, and alkyl-substituted ammonium salts of fluoride and chloride anions, and at least one solvent selected from the group consisting of acetonitrile, diethylene glycol dimethyl ether, and toluene/tetraalkylammonium fluoride; and mixtures thereof.

* * * * *

UNITED STATES PATENT AND TRADEMARK OFFICE
CERTIFICATE OF CORRECTION

PATENT NO. : 5,466,877
DATED : November 14, 1995
INVENTOR(S) : George G. I. Moore It is certified that error appears in the above-indentified patent and that said Letters Patent is hereby corrected as shown below:

Col. 1, line 14, "oil-)" should read -- oil- --.

Col. 4, line 5, delete "*preparations*" and insert --*Preparations*--.

Col. 5, line 1, after "[2.2.2" insert --]--.

Signed and Sealed this

Twenty-eighth Day of May, 1996

Attest:

BRUCE LEHMAN

*Attesting Officer*  *Commissioner of Patents and Trademarks*